United States Patent
Crowe et al.

[11] Patent Number: 5,858,725
[45] Date of Patent: Jan. 12, 1999

[54] PREPARATION OF CHIMAERIC ANTIBODIES USING THE RECOMBINANT PCR STRATEGY

[75] Inventors: James Scott Crowe; Alan Peter Lewis, both of Beckenham, England

[73] Assignee: Glaxo Wellcome Inc., Research Triangle Park, N.C.

[21] Appl. No.: 39,198

[22] PCT Filed: Oct. 8, 1990

[86] PCT No.: PCT/GB91/01744
§ 371 Date: Jul. 29, 1993
§ 102(e) Date: Jul. 29, 1993

[87] PCT Pub. No.: WO92/07075
PCT Pub. Date: Apr. 30, 1992

[30] Foreign Application Priority Data

Oct. 10, 1990 [GB] United Kingdom ............ 9022011

[51] Int. Cl.⁶ .............. C12N 5/10; C07K 16/46; C07H 21/04
[52] U.S. Cl. ............. 435/69.7; 435/70.21; 435/71.1; 435/69.1; 435/91; 435/252.3; 435/326; 530/387.3; 530/867; 536/23.53
[58] Field of Search ................ 435/69.7, 70.21, 435/71.1, 69.1, 91, 240.27, 252.3, 326; 536/23.53; 530/387.3, 867

[56] References Cited

FOREIGN PATENT DOCUMENTS 9007861  7/1990  WIPO .

OTHER PUBLICATIONS

Emery et al. [Exp. Opin. Invest. Drugs 3(3):241–251 (1994).
Colman, Research in Immunology, 145:33, 1994.
Horton, et al., *Gene,* 77 (1989), pp. 61–68.
Horton, et al., *Biotechniques,* 8(5) (May 1990), pp. 528–535.
Lewis, et al., *Gene,* 101:2 (1991), pp. 297–302.
LeBoeuf, et al., *Gene,* 82 (1989), pp. 371–377.

*Primary Examiner*—Frank C. Eisenschenk
*Attorney, Agent, or Firm*—Nixon & Vanderhye P.C.

[57] ABSTRACT

The invention relates to a method of producing a chimaeric antibody in which the CDR of a first antibody is spliced between the framework regions of a second antibody. The method is performed using a template comprising two framework regions, AB and CD, and between them, the CDR which is to be replaced by a donor CDR. Primers A and B are used to amplify the framework region AB, and primers C and D used to amplify the framework region CD. However, the primers B and C also contain, at their 5' ends, additional sequence corresponding to all or at least part of the donor CDR sequence. Primers B and C overlap by a length sufficient to permit annealing of their 5' ends to each other under conditions which allow a polymerase chain reaction to be performed and thereby incorporate all of the donor CDR sequence. The amplified regions AB and CD may undergo splice overlap extension to produce the chimaeric product in a single reaction.

9 Claims, 4 Drawing Sheets

Fig. 2

TEMPLATE

```
         HindIII              CAMPATH-1H Leader              CAMPATH-1H CH3           HindIII
                                    M                           P G K *
5'-AAGCTTTACAGTTACTGAGCACACAGGACCTCACC...117bp...TGCACCGTGTCTGGCTTCACCTTCACC...1206bp...CCGGGTAAATGAGTGCGACGAAGCTT-3'

CAMPATH-1H FRH1         CAMPATH-1H CDRH1      CAMPATH-1H FRH2
                     C T V S G F T F T       D F Y M N             W V R Q P P G R G
                     TGCACCGTGTCTGGCTTCACCTTCACC  GATTTCTACATGAAC  TGGGTGAGACAGCCACCTGGACGAGGT..
```

PRIMERS

```
        Primer A -->                                              Primer C -->
5'-GATCAAGCTTTACAGTTACTGAGC-3'                    5'-acttatggtatgggtgtgggcTGGGTGAGACAGCCACCTGACGA-3'
                                                       <-- Primer B
                                                  3'-TGGCACAGACCGTCGTGGAAGTGgaattataccacacccg-5'
              <-- Primer D
        3'-CATTTACTCACGCTGCCTTCGAACTAG-5'
```

FRAGMENT AB

```
5'-GATCAAGCTTTACAGTTACTGAGCACACAGGACCTCACCATG...117bp...TGCACCGTGTCTGGCCACCTTCAGCacttatggtatgggtgtgggc-3'
3'-CTAGTTCGAAATGTCAATGACTCGTGTGTCCTGGAGTGGTAC         AGCACAGACCGGTGGAAGTCGtgaatataccatacccacccg-5'
```

FRAGMENT CD

```
                                          5'-acttatggtatgggtgtgggcTGGGTGAGACAGCCACCTGACGAGGT...
                                          3'-tgaataccataccacacccgACCCACTCTGTCGGTGGACCTGCTCA ...1206bp...CCGGGTAAATGAGTGCGACGAAGCTTGATC-3'
            GGCCCATTTACTCACGCTGCTTCGAACTAG-5'
```

HindIII                CAMPATH-1H Leader              CAMPATH-1H FRH1*                    DX48 CDRH1            CAMPATH-1H FRH2
                                      M                        C T V S G(S) T F(S)                 t y g m g v g         W V R Q P P G R G

FRAGMENT AD

```
5'-GATCAAGCTTTACAGTTACTGAGCACACAGGACCTCACCATG...117bp...TGCACCGTGTCTGGCCAGCACCTTCAGCacttatggtatgggtgtgggcTGGGTGAGACAGCCACCTGACGAGT..
3'-CTAGTTCGAAATGTCAATGACTCGTGTGTCCTGGAGTGGTAC            AGTGGCACAGACCGGTCGTGGAAGTCGtgaataccataccacacccgACCCACTCTGTCGGTGGACCTGCTCCA CAMPATH-1H CH3          HindIII
                                  P G A *
              ...1206bp...CCGGGTAAATGAGTGCGACGAAGCTTGATC-3'
                          GGCCCATTTACTCACGCTGCTTCGAACTAG-5'
```

PREPARATION OF CHIMAERIC ANTIBODIES USING THE RECOMBINANT PCR STRATEGY

The present invention relates to the preparation of chimaeric antibodies. The invention is typically applicable to the production of humanised antibodies.

Antibodies typically comprise two heavy chains linked together by disulphide bonds and two light chains. Each light chain is linked to a respective heavy chain by disulphide bonds. Each heavy chain has at one end a variable domain followed by a number of constant domains. Each light chain has a variable domain at one end and a constant domain at its other end. The light chain variable domain is aligned with the variable domain of the heavy chain. The light chain constant domain is aligned with the first constant domain of the heavy chain. The constant domains in the light and heavy chains are not involved directly in binding the antibody to antigen.

The variable domains of each pair of light and heavy chains form the antigen binding site. The domains on the light and heavy chains have the same general structure and each domain comprises a framework of four regions, whose sequences are relatively conserved, connected by three complementarily determining regions (CDRs). The four framework regions largely adopt a beta-sheet conformation and the CDRs form loops connecting, and in some cases forming part of, the beta-sheet structure. The CDRs are held in close proximity by the framework regions and, with the CDRs from the other domain, contribute to the formation of the antigen binding site. CDRs and framework regions of antibodies may be determined by reference to Kabat et al ("Sequences of proteins of immunological interest" U.S. Dept. of Health and Human Services, U.S. Government Printing Office, 1987).

The preparation of an altered antibody in which the CDRs are derived from a different species to the variable domain framework regions is disclosed in EP-A-0239400. The CDRs may be derived from a rat or mouse monoclonal antibody. The framework of the variable domains, and the constant domains, of the altered antibody may be derived from a human antibody. Such a humanised antibody elicits a negligible immune response when administered to a human compared to the immune response mounted by a human against a rat or mouse antibody. Humanised CAMPATH-1 antibody is disclosed in EP-A-0328404.

The technique of "overlap extension" involves the use of oligonucleotide primers complementary to a template nucleotide sequence and the polymerase chain reaction (PCR) to generate DNA fragments having overlapping ends. These fragments are combined in a "fusion" reaction in which the overlapping ends anneal allowing the 3' overlap of each strand to serve as a primer for the 3' extension of the complementary strand. Ho et Al (Gene, 77, 51–59 (1989)) describe the use of this technique to introduce specific alterations in a nucleotide sequence by incorporating nucleotide changes into the overlapping oligo primers. Using this technique of site-directed mutagenesis, those variants of the mouse major histocompatibility complex class-I gene were generated cloned and analysed.

Horton et a (*Gene*, 77 61–68 (1989)) describe a technique of gene splicing by overlap extension (SOE). The technique allows the production of a hybrid length of DNA, AD, by splicing two pieces of DNA, AB and CD, which are produced by a PCR using primers A, B, C and D. At least part of the primers B and C are complementary to each other. The fragments AB and CD produced by PCR are mixed to allow the positive strand of AB to anneal to the negative strand of CD. The overlap between B and C allows the two strands to prime extension of each other. Primers A and D are used to prime a PCR reaction of the extended strands.

The above technique was used to splice a portion (CD) of the mouse $H-2K^b$ gene between upstream and downstream regions (AB and EF respectively) of the corresponding upstream and downstream parts of the $H-2L^d$ gene. All three fragments, AB, CD and EF were produced by PCR, using primers A to F. The three fragments were joined by two rounds of SOE, the first one producing a fragment AD (ie. AB-CD) and the second producing the product AF (ie. AB-CD-EF).

According to the present invention, a method has now been devised of producing a chimaeric antibody in which the CDR of a first antibody is spliced between the framework regions of a second antibody.

In general, the technique of the present invention is performed using a template comprising two framework regions, AB and CD, and between them, the CDR which is to be replaced by a donor CDR. Primers A and B are used to amplify the framework region AB, and primers C and D used to amplify the framework region CD. However, the primers B and C also contain, at their 5' ends, additional sequence corresponding to all or at least part of the donor CDR sequence. Primers B and C overlap by a length sufficient to permit annealing of their 5' ends to each other under conditions which allow a polymerase chain reaction (PCR) to be performed and thereby incorporate all of the donor CDR sequence. The amplified regions AB and CD may undergo SOE to produce the chimaeric product in a single reaction.

According to one aspect the present invention provides a method for producing a double- or single-stranded DNA of formula $$5'F1\text{-}M\text{-}F2\ 3'$$

encoding an antibody chain or fragment thereof in which at least one of the complementarity determining regions (CDRs) of the variable region of the antibody chain is derived from a first mammalian antibody, and the framework of the variable region is derived from a second, different mammalian antibody, wherein M comprises DNA encoding a CDR of the second antibody and F1 and F2 encode sequences flanking M, which method comprises;

(i) preparing a single- or double-stranded DNA template of the formula $$5'f1\text{-}H\text{-}f2\ 3'$$

wherein H comprises DNA encoding a CDR of a different specificity from M and f1 and f2 are substantially homologous to F1 and F2 respectively;

(ii) obtaining DNA oligonucleotide primers A, B, C and D wherein

A
  comprises a sequence $a^1$ which has a 5' end corresponding to the 5' end of F1 and which is identical to a corresponding length of the sequence F1,
  is oriented in a 5' to 3' direction towards H;

B consists of the sequence $$5'b^1\text{-}b^2\ 3'$$

wherein
  $b^1$ comprises a sequence complementary to a corresponding length of M and has a 3' end which is complementary to the 5' end of M, and $b^2$ is complementary to a sequence of corresponding length in F1 and has a 5' end which starts at the nucleotide complementary to the 3' end of F1;

C consists of the sequence $$5'c^1-c^2\ 3'$$

wherein $c^1$ comprises a sequence identical to the corresponding length of M and has a 3' end which corresponds to the 3' end of M, and $c^2$ is identical to a sequence of corresponding length in F2 and has a 5' end which starts at the nucleotide corresponding to the 5' end of F2;

D comprises a sequence $d^1$ which has a 5' end complementary to the 3' end of F2 and which is complementary to a corresponding length of F2, and is oriented in a 5' to 3' direction towards H;

and wherein $b^1$ and $c^1$ overlap by a length sufficient to permit annealing of their 5' ends to each other under conditions which allow a PCR to be performed;

(iii) performing, in any desired order, PCR reactions with primer pairs A,B and C,D on the template prepared in (i) above; and (iv) mixing the products obtained in (iii) above and performing a PCR reaction using primers A and D.

The oligonucleotides may be of any convenient size.

Preferably F1 and F2 each encode at least one human antibody framework region and optionally further CDRs. Preferably H encodes a CDR of said first antibody. Preferably M encodes a non-human CDR region, most preferably a murine or rodent CDR.

Primers A and D will usually be at least 12, for example at least 15 nucleotides, and more usually from 20 to 30 nucleotides in length. If desired primers A and D may contain at least one restriction endonuclease recognition site within nucleotides of their 5' ends. Primers B and C will usually be at least 20, for example at least 30 nucleotides in length. More usually, these primers will be over 40, for example 45 to 60 nucleotides long. It is generally possible to synthesise oligonucleotides of up to 200 nucleotides in length. Generally primers A, B, C and D will thus each be from 15 to 200 nucleotides in length.

The length of overlap between $b^1$ and $c^1$ may depend on a number of factors, including the total length of B and C and the particular base composition of the region of the overlap. However, the overlap will usually be at least 12, for example at least 15, nucleotides. According, to one embodiment, the sequences $b^1$ and $c^1$ within the primers B and C are the same number of nucleotides in length. In a preferred embodiment of the invention $b^1$ and $c^1$ are both the length of M and thus the overlap is also this length.

Usually, the distance between the 3' end of primer A and the 5' end of H will be at least 15 nucleotides. More usually, the distance will be the length of f1 minus the length of A itself. Similarly, the distance between the 3' end of D and the region H will also be at least 15 nucleotides, and more usually the length of f2 minus the length of D itself. According to one embodiment the sequences $a^1$, $b^2$, $c^2$ and $d^1$ of primers A, B, C and D respectively are each from 15 to 30 nucleotides in length.

It will be appreciated that the entire sequence of M and the 5' and 3' regions of F1 and F2 will be determined by the sequence of the primers A, B, C and D.

It is therefore considered inappropriate in this situation to refer to "homology" between these primers and any parts of the sequence F1, M or F2. Instead, the term "corresponding length" as used herein means a sequence of the same number of nucleotides and with the identical (or complementary) sequence.

With reference to step (i) above, the sequences f1 and f2 will be substantially homologous to F1 and F2 respectively in that the primers A to D may be used to introduce minor changes to f1 and f2 in the regions of these primer sequences.

The regions F1 and F2 comprise DNA encoding at least part of the framework regions either side of the CDR M. F1 and F2 may also encode regions flanking these sequences, for example into and beyond DNA encoding further CDRs.

According to another aspect, the present invention provides an oligonucleotide 30 to 110 nucleotides in length which consists of the sequence:

$$5'o^1-o^2\ 3'$$

wherein $o^1$ comprises at least 15 nucleotides of a sequence of a CDR region of non-human origin and $o^2$ comprises at least 15 nucleotides of a framework region of human origin. This oligonucleotide is suitable for use as a primer in the process described above.

According to a still further aspect, the present invention provides a method for producing a double- or single-stranded DNA of formula $$5'F1\text{-}M1\text{-}F2\text{-}M2\text{-}F3\text{-}M3\text{-}F4\ 3'$$

encoding an antibody chain or fragment thereof in which the three complementarity determining regions (CDRs) of the variable region of the antibody chain are derived from a first mammalian antibody, and the four framework regions of the variable domain are derived from a second, different mammalian antibody, wherein M1, M2 and M3 comprise DNA encoding CDRs of the second antibody and F1, F2, F3 and F4 comprise framework sequences flanking the CDRs M1, M2 and M3, which method comprises;

(i) preparing a single- or double-stranded DNA template of the formula $$5'f1\text{-}H1\text{-}f2\text{-}H2\text{-}f3\text{-}H3\text{-}f4\ 3'$$

wherein H1, H2 and H3 comprises DNA encoding CDRs of a different specificity from M1, M2 and M3, and f1, f2, f3 and f4 are substantially homologous to F1, F2, F3 and F4 respectively;

(ii) obtaining DNA oligonucleotide primers A, B, C, D, E, F, G and H wherein

A
comprises a sequence $a^1$ which has a 5' end corresponding to the 5' end of F1 and which is identical to a corresponding length of the sequence F1, is oriented in a 5' to 3' direction towards H1;

B consists of the sequence $$5'b^1-b^2\ 3'$$

wherein $b^1$ comprises a sequence complementary to a corresponding length of M1 and has a 3' end which is complementary to the 5' end of M1, and b2 is complementary to a sequence of corresponding length in F1 and has a 5' end which starts at the nucleotide complementary to the 3' end of F1;

C consists of the sequence $$5'c^1\text{-}c^2\ 3'$$

wherein
$c^1$ comprises a sequence identical to the corresponding length of M1 and has a 3' end which corresponds to the 3' end of M1, and
$c^2$ is identical to a sequence of corresponding length in F2 and has a 5' end which starts at the nucleotide corresponding to the 5' end F2;

D consists of the sequence $$5'd^1\text{--}d^2\ 3'$$

wherein
$d^1$ comprises a sequence complementary to a corresponding length of M2 and has a 3' end which is complementary to the 5' end of M2, and
$d^2$ is complementary to a sequence of corresponding length in F2 and has a 5' end which starts at the nucleotide complementary to the 3' end of F2;

E consists of the sequence $$5'e\text{--}e^2\ 3'$$

wherein
$e^1$ comprises a sequence identical to the corresponding length of M2 and has a 3' end which corresponds to the 3' end of M2, and
$e^2$ is identical to a sequence of corresponding length in F3 and has a 5' end which starts at the nucleotide corresponding to the 5' end F3;

F consists of the sequence $$5'f\text{--}f^2\ 3'$$

wherein
$f^1$ comprises a sequence complementary to a corresponding length of M3 and has a 3' end which is complementary to the 5' end of M3, and
$f^2$ is complementary to a sequence of corresponding length in F3 and has a 5' end which starts at the nucleotide complementary to the 3' end of F3;

G consists of the sequence $$5'g^1\text{--}g^2\ 3'$$

wherein
$g^1$ comprises a sequence identical to the corresponding length of M3 and has a 3' end which corresponds to the 3' end of M3, and
$g^2$ is identical to a sequence of corresponding length in F4 and has a 5' end which starts at the nucleotide corresponding to the 5' end F4;

H
comprises a sequence $h^1$ which has a 5' end complementary to the 3' end of F4 and which is complementary to a corresponding length of F4, and
is oriented in a 5' to 3' direction towards H3;
and wherein the pairs $b^1$ and $c^1$, $d^1$ and $e^1$, and $f^1$ and $g^1$ overlap by a length sufficient to permit annealing of their 5' ends to each other under conditions which allow a PCR to be performed;

(iii) performing, in any desired order, PCR reactions with primer pairs A,B; C,D; E,F and G,H on the template prepared in (i) above to obtain DNA fragments AB, CD, EF and GH; and (iv) splicing the fragments obtained in (iii) above to obtain the desired DNA.

According to one embodiment, F4 comprises the framework sequence flanking the CDR M3 and DNA encoding all or part of the constant region of the antibody chain.

Step (iv) may be performed by:
(iva) mixing fragments AB and CD with primers A and D and performing a PCR to obtain a DNA fragment AD;
(ivb) mixing, before, during or following step (iva) above, fragments EF and GH with primers E and H and performing a PCR to obtain a DNA fragment EH; and
(ivc) mixing fragments AD and EH with primers A and H to obtain the desired DNA.

Alternatively step (iv) may be performed by:
(iva) mixing fragments CD and EF with primers C and F and performing a PCR to obtain a DNA fragment CF; and EITHER:
(ivb-1) mixing fragments AB and CF with primers A and F and performing a PCR to obtain a DNA fragment AF; and
(ivc-1) mixing fragments AF and GH with primers A and H to obtain the desired DNA; OR:
(ivb-2) mixing fragments CF and GH with primers C and H and performing a PCR to obtain a DNA fragment CH; and
(ivc-2) mixing fragments AB and CH with primers A and H to obtain the desired DNA.

DESCRIPTION OF THE DRAWINGS

FIG. 2 shows in detail the key sequences involved in the process illustrated in FIG. 1 (SEQ ID NO:1 to SEQ ID NO:8).

Figure 1:
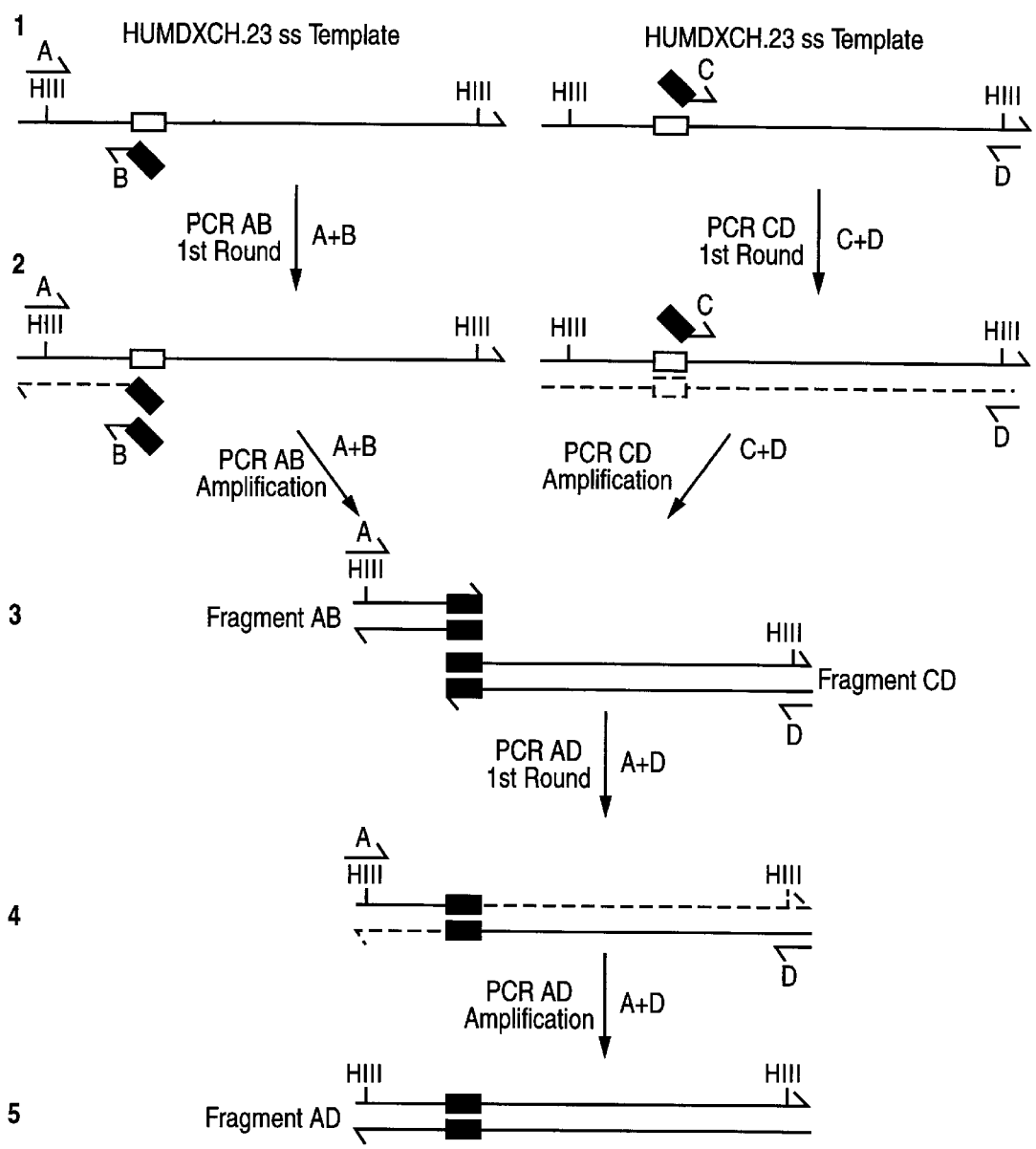
FIG. 1 illustrates a process according to the present invention. The dark box indicates DNA sequence from a murine CDR region which is inserted between framework regions of the CAMPATH antibody, replacing the original CDR (unshaded box). A, B, C and D indicate the PCR primers used, with half-arrows indicating their 5' to 3' orientation.
Figure 3:
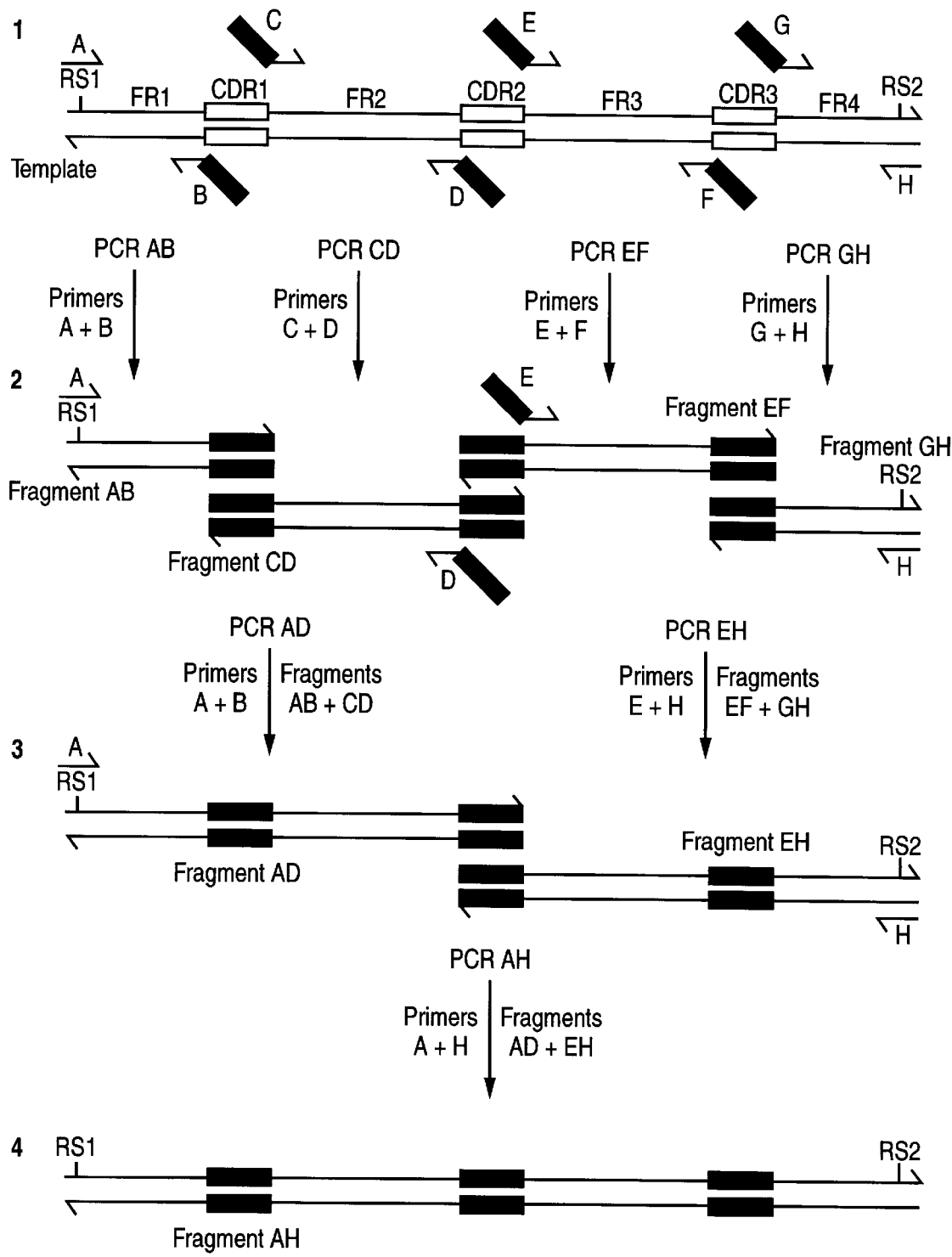
FIG. 3 is a schematic illustration of how the process of the invention may be used to replace all three CDR regions of an antibody.

Possible variations in the F1 and F2 DNA regions are apparent by contrasting the embodiments of the invention illustrated in FIGS. 1 and 3.

In FIG. 1, a process according to the invention is illustrated showing the replacement of a single CDR DNA.

The region F2 in FIG. 1 is between primers "C" and "D", starting at the 5' end of $c^2$ as defined above to the complement of the 5' end of "D". This region encodes a total of 3 framework regions, 2 CDRs and the whole heavy chain constant region incorporating a stop codon within primer D. In contrast, the DNA of F1, 5' to the CDR being replaced, contains a single framework and no CDRs.

In FIG. 3, the DNA between primers "C" and "D" encodes a single framework region. This is because the process illustrated shows the replacement of all 3 CDRs of DNA encoding the variable region of an antibody. With this arrangement, it should be noted that primer "D" comprises not only the sequence of $d^1$ but also additional 5' sequence encoding part of a second CDR region.

When the DNA encoding all 3 CDRs of an antibody chain is to be replaced, the arrangement of FIG. 3 may be used.

Thus, a first set of 4 primers, "A", "B", "C" and "D" (as defined above for A, B, C and D) are used to replace all of a first CDR (CDR1) and at least part of a second CDR, (CDR2). A second set of primers, "E", "F", "G" and "H" (defined as for A, B, C and D respectively) are used to replace a third CDR (CDR3) and at least part of CDR2. In order to ensure the replacement of CDR2, primers "D" and "E" must overlap by a length sufficient to permit annealing of their 5' ends to each other under conditions which allow a PCR to be performed. In essence, replacement of CDR2 is accomplished by a set of four primers, "C", "D", "E" and "F", defined as for A, B, C and D respectively.

In the embodiment of the invention illustrated by FIG. 3, fragments AB and CD are annealed to provide fragment AD, and fragments EF and GH are spliced to provide fragment EH. Finally AD is spliced with EH to provide fragment AH, encoding a variable region in which all 3 CDRs are replaced.

Other arrangements by which all 3 CDR DNAs may be replaced in a DNA encoding a variable region using primers "A" to "H" as illustrated in FIG. 3 include performing reactions with primer pairs "A"+"B", "C"+"D", "E"+"F" and "G"+"H" as illustrated in FIG. 3(1), splicing fragments CD and EF together to produce a fragment CF, and splicing this fragment with either first fragment AB and then GH, or vice versa.

Alternatively, the DNA encoding the 3 CDRs may be replaced sequentially. A first reaction using primers "A", "B", "C" and "H" (as shown in FIG. 3 and defined as for primers A to D) may be used to replace CDR1, in accordance with the present invention. A second set of reactions, using primers "A", "E", "D" and "H" (as shown in FIG. 3 and defined as for primers A to D) replaces CDR2. A final set of reactions, using primers "A", "F", "G" and "H" replaces CDR3.

The primers A and D may also, at their 5' ends contain additional sequences which represent, for example, restriction endonuclease recognition sequences not represented in f1 or f2.

The sequences of A and D 5' to $a^1$ and $d^1$ will be ignored when considering the degree of homology between f1 and F1, and f2 and F2. Similarly, if F1 and/or F2 are shorter than f1 and/or f2 respectively, the additional sequences of f1/f2 for which F1/F2 have no counterpart will also be ignored when measuring the degree of homology.

All the primers may contain a number, for example 1 to 10, such as 2 to 5 nucleotide mismatches between the f1/f2 sequences and the corresponding or complementary primer sequences. These mismatches may be used to design desired coding changes in the sequences of F1 and F2 when compared with f1 and f2.

The process of the invention may be used to produce a chimaeric antibody or fragment thereof in which any one of the CDR regions are replaced. It may also be used to replace any two, or all three CDR regions of an antibody variable region.

The process of the invention may be used to replace the DNA encoding one or more CDRs of a complete antibody light or heavy chains. Fragments of DNA encoding at least one CDR region may be used. For example, it is possible to produce antibody fragments such as Fab, F(ab)$_2$ or Fv fragments, in which the DNA encoding one or both of the light or heavy chains has been subjected to the process of the invention.

DNA encoding framework regions and CDRs of antibodies will often be present in a vector, for example an expression vector. In some cases, it will be necessary or desirable that one or both of the primers A and D (or at least their regions $a^1$ and $d^1$) correspond to vector sequences, rather than sequences of one of the framework regions flanking the CDR being replaced.

The DNA produced according to the invention may be cloned into any suitable replication or expression vector and introduced into a bacterial, yeast, insect or mammalian cell to produce chimaeric antibody. Examples of suitable systems for expression are described below.

The antibody chain may be co-expressed with a complementary antibody chain. At least the framework of the variable region and the or each constant region of the complementary chain generally are derived from the said second species also. A light chain and a heavy chain may be co-expressed. Either or both-chains may have been prepared by the process of the invention. Preferably the CDRs of both chains are derived from the same selected antibody. An antibody comprising both expressed chains can be recovered.

The antibody preferably has the structure of a natural antibody or a fragment thereof. The antibody may therefore comprise a complete antibody, a (Fab')$_2$ fragment, a Fab fragment, a light chain dimer or a heavy chain. The antibody may be an IgG, such as an IgG1, IgG2, IgG3 or IgG4 IgM, IgA, IgE or IgD. Alternatively, the antibody may be a chimaeric antibody of the type described in WO 86/01533.

A chimaeric antibody according to WO 86/01533 comprises an antigen binding region and a non-immunoglobulin region. The antigen binding region is an antibody light chain variable region or heavy chain variable region. Typically, the chimaeric antibody comprises both light and heavy chain variable regions. The non-immunoglobulin region is fused at its C-terminus to the antigen binding region. The non-immunoglobulin region is typically a non-immunoglobulin protein and may be an enzyme region, a region derived from a protein having known binding specificity, from a protein toxin or indeed from any protein expressed by a gene. The two regions of the chimaeric antibody may be connected via a cleavable linker sequence.

The invention is preferably employed to humanise an antibody, typically a monoclonal antibody and, for example, a rat or mouse antibody. The framework and constant regions of the resulting antibody are therefore human framework and constant regions whilst the CDRs of the light and/or heavy chain of the antibody are rat or mouse CDRs. Preferably all CDRs are rat or mouse CDRs. The antibody produced in accordance with the present invention may be a human IgG such as IgG1, IgG2, IgG3, IgG4; IgM; IgA; IgE or IgD carrying rat or mouse CDRs.

The process of the invention is carried out in such a way that the resulting chimaeric antibody retains the antigen binding capability of the non-human antibody from which the CDR region(s) is/are derived.

The starting antibody is typically an antibody of a selected specificity. In order to ensure that this specificity is retained, the variable region framework of the antibody is preferably the closest variable region framework of an antibody of another species. By "about the closest" is meant about the most homologous in terms of amino acid sequences. Preferably there is a homology of at least 50% between the two variable regions.

There are four general steps to produce a humanised antibody by the method according to the invention. These are:

(1) determining the nucleotide and predicted amino acid sequence of the starting antibody light and heavy chain variable regions;

(2) designing the chimaeric antibody, i.e. deciding which antibody framework region to use during the process;

(3) identifying the oligonucleotides A, B, C, and D and use of these primers in a series of PCR reactions to produce DNA encoding the humanised antibody; and (4) the transfection of a suitable host cell line with the DNA and expression of the humanised antibody.

These four steps are explained below in the context of humanising an antibody. However, they may equally well be applied when reshaping to an antibody of a non-human species.

Step 1: Determining the nucleotide and predicted amino acid sequence of the antibody light and heavy chain variable regions To make a chimaeric antibody only the amino acid sequence of antibody's heavy and light chain variable regions needs to be known. The sequence of the constant regions is irrelevant because these do not contribute to the humanising strategy. The simplest method of determining the variable region amino acid sequence of an antibody is from cloned cDNA encoding the heavy and light chain variable region.

There are two general methods for cloning heavy and light chain variable region cDNAs of a given antibody: (1) via a conventional cDNA library, or (2) via PCR. Both of these methods are widely known. Given the nucleotide sequence of the cDNAs, it is a simple matter to translate this information into the predicted amino acid sequence of the antibody variable regions.

Step 2: Designing the chimaeric antibody

There are several factors to consider in deciding which human antibody sequence to use during the humanisation. The humanisation of light and heavy chains are considered independently of one another, but the reasoning is basically similar for each.

This selection process is based on the following rationale: A given antibody's antigen specificity and affinity is primarily determined by the amino acid sequence of the variable region CDRs. Variable region framework residues have little or no direct contribution. The primary function of the framework regions is to hold the CDRs in their proper spacial orientation to recognize antigen. Thus the substitution of rodent CDRs into a human variable region framework is most likely to result in retention of their correct spacial orientation if the human variable region is highly homologous to the rodent variable region from which they originated. A human variable region should preferably be chosen therefore that is highly homologous to the rodent variable region(s).

A suitable human antibody variable region sequence can be selected as follows:

1. Using a computer program, search all available protein (and DNA) databases for those human antibody variable region sequences that are most homologous to the rodent antibody variable regions. The output of a suitable program is a list of sequences most homologous to the rodent antibody, the percent homology to each sequence, and an alignment of each sequence to the rodent sequence. This is done independently for both the heavy and light chain variable region sequences. The above analyses are more easily accomplished if only human immunoglobulin sequences are included.

2. List the human antibody variable region sequences and compare for homology. Primarily the comparison is performed on length of CDRs, except CDR3 of the heavy chain which is quite variable. Human heavy chains and Kappa and Lambda light chains are divided into subgroups; Heavy chain 3 subgroups, Kappa chain 4 subgroups, Lambda chain 6 subgroups. The CDR sizes within each subgroup are similar but vary between subgroups. It is usually possible to match a rodent Ab CDR to one of the human subgroups as a first approximation of homology. Antibodies bearing CDRs of similar length are then compared for amino acid sequence homology, especially within the CDRs, but also in the surrounding framework regions. The human variable region which contains -he most homologous CDRs is chosen as the framework for humanisation.

Step 3: Identification and use of the oligonucleotides A, B, C and D

The general principles for designing primers for PCR are well known, eg. as described by R. K. Saiki ("The Design and Optimisation of the PCR" in "PCR Technology", Ed H. A. Erlich, Stockton Press, (1989)). In addition, specific factors can be considered for each CDR replacement. Where necessary, or desired, the 5' ends of A and/or D may encode part or all of a second and/or third CDR. The primers, A and D, may also include at their 5' ends restriction enzyme sites. These sites can be designed according to the vector which will be used to clone the humanised antibody from the final PCR reaction. The primers B and C must be long enough to overlap by at least a length sufficient to permit annealing of their 5' ends to each other under conditions which allow a PCR to be performed. This will usually require an overlap of at least 12, and preferably at least 15 nucleotides. One or more of the four primers may differ from their template sequences by one or more nucleotides. These differences may be used to introduce desired coding changes into the framework regions of the antibody.

The primers are then used in a series of PCR reactions using the appropriate template to generate the DNA encoding the humanised antibody. PCR reactions may be carried out as described by Saiki et al, *Science,* 29, 487–491 (1988). At each stage the desired product of the PCR reaction may be purified as necessary, for example using selective filtration and if necessary the identity of the product can be established, for example by gel electrophoresis.

Stem 4: Transfection and expression of the reshaped antibody

Following the reactions to produce the DNA encoding the chimaeric antibody, the DNAs are linked to the appropriate DNA encoding light or heavy chain constant region, cloned into an expression vector, and transfected into a suitable host cell line, preferably a mammalian cell line. These stems can be carried out in routine fashion. A chimaeric antibody may therefore be prepared by a process comprising:

a) preparing a first replicable expression vector including a suitable promoter operably linked to a DNA sequence which encodes at least a variable region of an Ig heavy or light chain, the variable region comprising framework regions from a first antibody and CDRs from a second antibody of different specificity;

b) if necessary, preparing a second replicable expression vector including a suitable promoter operably linked to a DNA sequence which encodes at least the variable region of a complementary Ig light or heavy chain respectively;

c) transforming a cell line with the first or both prepared vectors; and d) culturing said transformed cell line to produce said altered antibody.

Preferably the DNA sequence in step a) encodes both the variable region and the or each constant region of the antibody chain. The antibody can be recovered and purified. The cell line which is transformed to produce the altered antibody may be a Chinese Hamster ovary (CHO) cell line or an immortalised mammalian cell line, which is advantageously of lymphoid origin, such as a myeloma, hybridoma, trioma or quadroma cell line. The cell line may also comprise a normal lymphoid cell, such as a B-cell, which has been immortalised by transformation with a virus, such as the Epstein-Barr virus. Most preferably, the immortalised cell line is a myeloma cell line or a derivative thereof.

Although the cell line used to produce the chimaeric antibody is preferably a mammalian cell line, any other suitable cell line, such as a bacterial cell line or a yeast cell line, may alternatively be used. In particular, it is envisaged that *E. coli*—derived bacterial strains could be used.

It is known that some immortalised lymphoid cell lines, such as myeloma cell lines, in their normal state secrete isolated Ig light or heavy chains. If such a cell line is transformed with the vector prepared in step (a) it will not be necessary to carry out step (b) of the process, provided that the normally secreted chain is complementary to the variable region of the Ig chain encoded by the vector prepared in step (a).

However, where the immortalised cell line does not secrete or does not secrete a complementary chain, it will be necessary to carry out step (b) This step may be carried out by further manipulating the vector produced in step (a) so that this vector encodes not only the variable region of a chimaeric antibody light or heavy chain, but also the complementary variable region.

Alternatively, step (b) is carried out by preparing a second vector which is used to transform the immortalised cell line. This alternative leads to easier construct preparation, but may not be as preferred as the first alternative in that production of antibody may be less efficient.

In the case where the immortalised cell line secretes a complementary light or heavy chain, the transformed cell line may be produced for example by transforming a suitable bacteria cell with the vector and then fusing the bacterial cell with the immortalised cell line by spheroplast fusion. Alternatively, the DNA may be directly introduced into the immortalised cell line by electroporation or other suitable method.

An antibody is consequently produced in which CDRs of a variable region of an antibody chain are homologous with the corresponding CDRs of an antibody of a Faust mammalian species and in which the framework of the variable region and the constant regions of the antibody are homologous with the corresponding framework and constant regions of an antibody of a second, different, mammalian species. Typically, all three CDRs of the variable region of a light or heavy chain are derived from the first species.

The antibody may be an IgG, such as IgG1, IgG2, IgG3 or IgG4 IgM, IgA, IgE or IgD. Alternatively, the antibody may be a chimaeric antibody of the type described in WO 86/01533.

Figure 4:
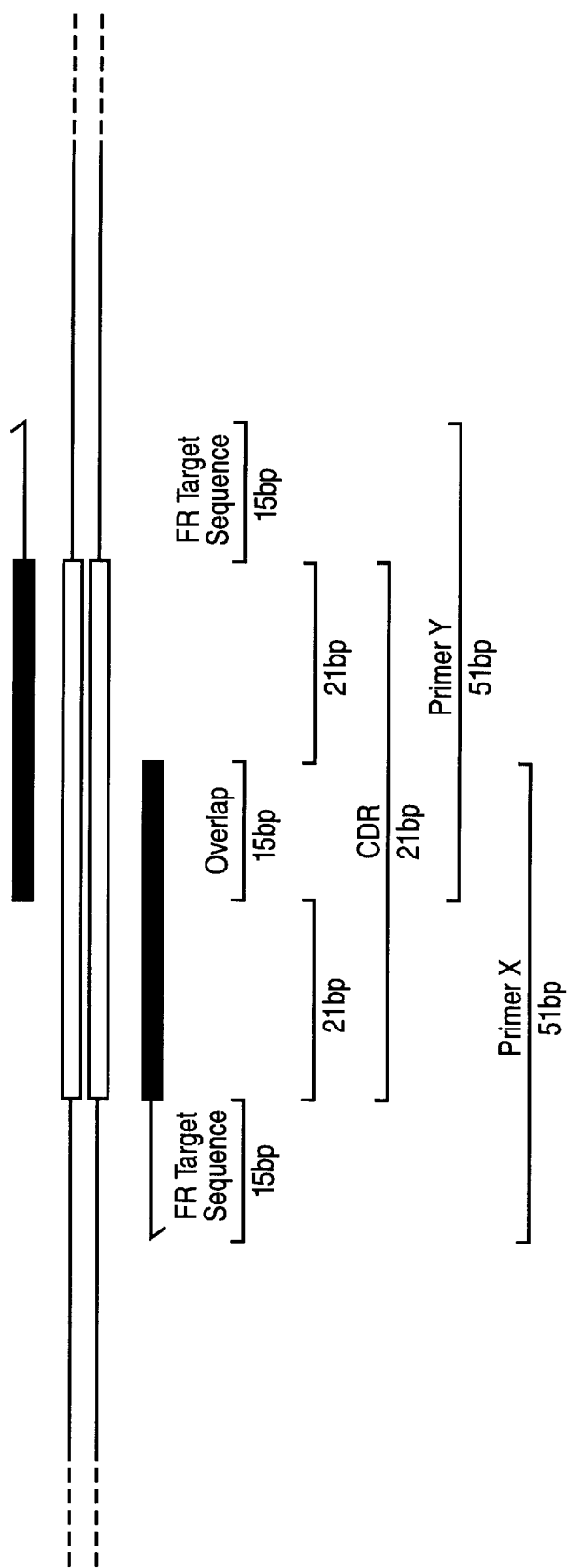
FIG. 4 illustrates in further detail one configuration of primers which may be used in the present invention.

The recombinant PCR technique of the present invention should allow the generation of fully humanised MAb DNA sequences in only two days using three rounds of PCR reactions (FIG. 3). Site-directed mutagenesis (Jones et al., *Nature,* 321, 522–525 (1986); Riechmann et al., *Nature,* 332, 323–327 (1988)) and oligonucleotide gene synthesis (Queen et al., *Proc. Natl. Acad. Sci. U.S.A.,* 86, 10029–10033 (1989)) have previously been used for the humanisation of antibodies. The above method has benefits over these techniques in that smaller oligonucleotides are required in the procedure, even to transfer large CDRs such as the 19 amino acid CDRH2 present in a number of human IgG subgroup III heavy chains (Cleary et al., *Cell,* 44, 97–106 (1986)). For example, as illustrated in FIG. 4, where the primary PCR products are designed to overlap in the middle of the CDR by 15 bp, the transfer of a 57 bp CDR onto the appropriate FR requires oligonucleotides of a maximum of 51 bp, assuming a homology of 15 bp corresponding to the FR target sequence (Higuchi, Using PCR to engineer DNA, in "PCR Technology" Ed. H. A. Erlich, Stockton Press (1989)).

The technique of the invention is also advantageous over site-directed mutagenesis in that all operations can be performed upon ds DNA without the need for subcloning between ds and ss vectors, thus decreasing the time and effort required to generate the humanised product.

The invention is illustrated by the following example.

EXAMPLE 1

(a) Recombinant PCR grafting of DX48 CDRH1 onto a human background

The objective was to graft a heavy chain CDR1 (CDRH1) from a rat anti-digoxin mAb (DX48) onto a human Ig backbone. The template used for the recombinant PCR was the previously humanised CAMPATH-1H heavy chain (Riechmann et al., *Nature,* 332, 323–327 (1988)), a human IgGl heavy chain with NEW (Saul et al.,*J. Biol. Chem.* 253, 585–597 (1978)) V region, which had been re-engineered from genomic into cDNA configuration, and had subsequently undergone site-directed mutagenesis to replace CAMPATH-1H CDRH2 and CDRH3 sequences with rat DX48 CDRH2 and CDRH3 yielding HUMDXCH.23 ss template in M13 (SEQ ID NO: 1).

PCR reactions (Saiki et al., *Science,* 239, 487–491 (1988)) were carried out using ss HUMDXCH.23 template prepared by the method of Sambrook at al., Molecular Cloning: A Laboratory Manual, 2nd Edn., Cold Spring Harbor Laboratory (1989). The reactions were performed in a programmable heating block (Hybaid) using 25 rounds of temperature cycling (94° C. for 1 min, 50° C. for 2 min, and 72° C. for 3 min) followed by a final 10 min step at 72° C. 1 µg of each primer, 50 ng of template and 2.5 Units of Taq polymerase (Perkin Elmer Cetus) were used in a final volume of 100 µl with the reaction buffer as recommended by the manufacturer. Synthetic oligonucleotides were made on a 7500 DNA Synthesizer (Milligen).

The approach used is summarised in FIG. 1. Primers used:
  A: SEQ ID NO: 2:
  B: SEQ ID NO: 3:
  C: SEQ ID NO: 4:
  D: SEQ ID NO: 5:

Two PCR reactions were carried out using the primer pairs A and B, and C with D respectively. Primers A and D correspond to positive and negative strand oligonucleotides incorporating the HindIII sites at the 5' and 3' termini of the HUMDXCH.23 insert. FIG. 2 shows the nucleotide sequence of three regions of the HUMDXCH.23 insert incorporating; the first 42 bp at the 5' end of the insert including the start codon of the CAMPATH-1H leader sequence; the 3' 27 bp of FRH1, the whole length of CDRH1 and the 5' 27 bp of FRH2 from CAMPATH-1H; and the final 27 bp at the 3' terminus of the insert including the stop codon at the end of CAMPATH-1H constant region (CH3). The sequences are separated by 117 bp and 1206 bp respectively. Primer B possesses negative strand sequence from the 3' end of the CAMPATH-1H FRH1 region (with point mutations to convert the 27 and Thr 30 of CAMPATH-1H back to the Ser residues present in the NEW FRH[1]) together with CDRH1 sequence of DX48 in place of the CAMPATH-1H CDRH1 (FIG. 2). Primer C is made up of the positive strand sequence of DX48 CDRH1, complementary to the CDRH1 region of primer B, running into the 5' end of the Campath-1H FRH2 (FIG. 2). In the first round of the AB and CD PCR reactions the HUMDXCH.23 negative strand is synthesised from primers B and D respectively (FIG. 1) in subsequent cycles fragments AB and CD (SEQ ID NO: 6 AND NO: 7 respectively) are amplified (FIGS. 1 and 2). The products of the two reactions thus constitute the whole length of the HUMDXCH-23 insert but with the point mutations stated above and the Campath-1H CDRH1 replaced by the CORH1 sequence of DX48. Fragments AB and CD both possess the DX48 CDRH1 sequence such that on denaturation and reannealing the overlapping sequences can anneal.

Excess primers were removed from the AB and CD PCR reactions by selective filtration on a Centricon 100 (Higuchi et al., Nucl. Acids Res., 16, 7351–7367 (1988); Amicon). 50 µl of each reaction was placed into 2 ml of TE (10 m Tris-HCl pH 8, 0.1 mM EDTA) and mixed in the upper reservoir of the Centricon 100. The manufacturer's protocol was followed using a 25 min centrifugation in a fixed-angle rotor at 1000×G, and the PCR products recovered in a 40 µl retentate.

10 µl of the Centricon 100 retentate was subjected to a recombinant PCR reaction with primers A and D (FIG. 1) using the same conditions as performed in the primary PCR reactions above. The positive strand of fragment AB and the negative strand of CD contain the complementary DX48 CDRH1 sequences at their 3' ends, and in the first PCR cycle can anneal and serve as primers for one another. Extension of the overlap produces the recombinant product fragment AD containing the transplanted DX48 CDRH1, and this is amplified by primers A and D in the subsequent rounds of PCR (FIGS. 1 and 2). The remaining strands of fragments AB and CD, which are complementary at their 5' ends, are not able to prime each other, but can act as templates for primers A and D. These generate more of the primary PCR products, although these fragments are not amplified in an exponential manner due to the absence of primers B and C in the reaction.

Gel-purified PCR products were analysed on an agarose gel containing 0.8% Type II: Medium EEO Agarose (Sigma) in 89 mM Tris-borate/2 mM EDTA, and visualised by staining with ethidium bromide. The expected sizes of the fragments were as follows: AB, 207 bp; CD, 1285 bp; AD, 1471 bp. The predominant band observed in each case was of the expected size, although additional minor bands also appeared in reaction AD.

(b) Cloning and sequencing of the recombinant PCR product

Fragment AD (SEQ ID NO: 8) was gel eluted, digested with HindIII (BRL) and cloned into the HindIII site of pUC-18 (BRL). The nucleotide sequence of a clone containing the recombinant molecule was determined by plasmid priming following the dideoxy chain-termination method (Sanger et al., *Proc. Natl. Acad. Sci. U.S.A.*, 74, 5463–5467 (1977)) according to the Sequenase kit (USB) protocol. The entire 1463 nt insert was found to be of the correct sequence, no misincorporations having resulted from the two sets of PCR reactions.

EXAMPLE 2

This objective was the humanisation of YFC51.1.1 rat anti-human -CD18 heavy and light chains. The DNA sequence of the variable regions of both chains had been determined and is shown in SEQ ID NOS 9 and 10—heavy chain and SEQ ID NOS 11 and 12—light chain.

Using the selection procedure described in Step (2) above, the human variable domain frameworks of the NEWM heavy chain and REI light chain (Kabat et al, "Sequences of proteins of immunological interest", U.S. Dept. of Health and Human Services, U.S. Government Printing Office (1987)) were chosen for the humanisation process.

The humanised heavy and light chains were constructed as follows.

(i) Light Chain

Light chain oligonucleotide primers:

$A_L$: SEQ ID NO: 13:
$B_L$: SEQ ID NO: 14:
$C_L$: SEQ ID NO: 15:
$D_L$: SEQ ID NO: 16:
$E_L$: SEQ ID NO: 17:
$F_L$: SEQ ID NO: 18:
$G_L$: SEQ ID NO: 19:
$H_L$: SEQ ID NO: 20:

PCR reactions were performed in a programmable heating block (Hybaid) using 20 rounds of temperature cycling (94° C. for 1 min, 50° C. for 2 min, and 72° C. for 3 min) followed by a final 10 min step at 72° C. 1 µg of each primer, a specified amount of template, and 2.5 units of Taq polymerase (Perkin Elmer Cetus) were used in a final volume of 100 µl with the reaction buffer as recommended by the manufacturer.

The initial template for the PCR was CAMPATH-1H light chain (humanised CAMPATH-1 on RE1 framework; Page and Sydenham, Biotechnology 9, 64–68, (1991)) Four initial PCR reactions were carried out, with long of template per reaction, using the primer pairs $A_L$ with $B_L$, $C_L$ with $D_L$, $E_L$ with $F_L$, and $G_L$ with $H_L$ respectively. The products of these PCR reactions, fragments $AB_L$, $CD_L$, $EF_L$ and $GH_L$ respectively, were purified using Prep-A-Gene (Bio-Rad) following the protocol recommended by the manufacturer. Fragments $AB_L$ with $CD_L$, and $EF_L$ with $GH_L$ were combined using a quarter of each purified product, and subjected to recombinant PCR reactions with primers $A_L$ plus $D_L$, and $E_L$ plus $H_L$ respectively. The products of these reactions, fragments $AD_L$ and $EH_L$, were purified as above, and a quarter of each combined in a recombinant PCR reaction using primers $A_L$ and $H_L$. The final humanised light chain recombinant PCR product, $AH_L$, was cloned into the HindIII site of pUC-18 (BRL) following the method of Crowe et al. (1991), utilising the HindIII sites in primers $A_L$ and $H_L$. Plasmid isolates were sequenced by the dideoxy chain termination method, and clones of the correct sequence chosen.

(ii) Heavy Chain

Heavy chain oligonucleotide primers:

$A_H$: SEQ ID NO: 21:
$B_H$: SEQ ID NO: 22:
$C_H$: SEQ ID NO: 23:
$D_H$: SEQ ID NO: 24:
$E_H$: SEQ ID NO: 25:
$F_H$: SEQ ID NO: 26:
$G_H$: SEQ ID NO: 27:
$H_H$: SEQ ID NO: 28:

The initial template for the PCR was CAMPATH-1H heavy chain. The rodent CDR's were grafted on to the template using the recombinant PCR method as described in section (i) but using oligonucleotide primers $A_H$ to $H_H$. The final PCR, i. e. fragments $AD_H$ and $EH_H$ with primers $A_H$ and $H_H$, did not give a high yield of product so a fragment AF, was generated (from fragments $AD_H$ and $EF_H$) and used with fragment $EH_H$ in a PCR with primers $A_H$ and $H_H$.

Oligonucleotides $A_H$ and $H_H$ were designed with HindIII and EcoRI sites respectively to enable initial cloning of the humanised variable region, and a SpeI site was introduced into the NEWM framework 4 (FR4) region of oligonucleotide $G_H$ to facilitate subsequent cloning of the variable region with a suitable constant region of choice. The SpeI site was chosen so as not to alter the leucine residue at position 109 (numbering according to Kabat et al, ibid) of the humanised heavy chain template. Four out of the six human heavy J-minigenes possess a leucine at this position; Kabat et al ibid). Thus the use of the engineered SpeI site should be generally applicable.

The humanised heavy chain variable region recombinant PCR product was cloned into HindIII/EcoRI-cut pUC-18 (BRL), and plasmid isolates of the correct sequence were chosen. The FR4 and γ1 constant regions of CAMPATH-1H heavy chain were PCR cloned into pUC-18 (BRL) using oligonucleotide primers XH (SEQ ID NO: 29) and YH (SEQ ID NO: 30). Primer $X_H$ contains SpeI and HindIII sites, and $Y_H$ an EcoRI site. The HINDIII and EcoRI sites were used to clone the PCR product into pUC-18, and plasmid isolates of the correct sequence were selected. The complete heavy chain was subsequently reconstituted from the humanised variable region and γ1 constant region clones using the engineered FR4 SpeI site.

---

We claim:

1. A method for producing a double- or single-stranded DNA of formula $$5'F1\text{-}M\text{-}F2\ 3'$$

encoding an antibody chain or fragment thereof in which of the complementarity determining regions (CDRs) of the variable region of the antibody chain is derived from a first mammalian antibody, and the framework of the variable region is derived from a second, different mammalian antibody, wherein M comprises DNA encoding a CDR of the second antibody and F1 and F2 respectively encode 5' and 3' sequences flanking M, which method comprises;

(i) preparing a single- or double-stranded DNA template of the formula $$5'f1\text{-}H\text{-}f2\ 3'$$

wherein H comprises DNA encoding a CDR of a different specificity from M and f1 and f2 are substantially homologous to F1 and F2 respectively;

(ii) obtaining DNA oligonucleotide primers A, B, C and D wherein

A comprises a sequence $a^1$ which has a 5' end corresponding to the 5' end of F1 and which is identical to a corresponding length of the sequence F1, is oriented in a 5' to 3' direction towards H;

B consists of the sequence $$5'b^1\text{-}b^2\ 3'$$

wherein $b^1$ comprises a sequence complementary to a corresponding length of M and has a 3' end which is complementary to the 5' end of M, and $b^2$ is complementary to a sequence of corresponding length in $F^1$ and has a 5' end which starts at the nucleotide complementary to the 3' end of $F^1$;

C consists of the sequence $$5' c^1 - c^2 \ 3'$$

wherein $c^1$ comprises a sequence identical to the corresponding length of M and has a 3' end which corresponds to the 3' end of M, and $c^2$ is identical to a sequence of corresponding length in F2 and has a 5' end which starts at the nucleotide corresponding to the 5' end of F2;

D comprises a sequence $d^1$ which has a 5' end complementary to the 3' end of F2 and which is complementary to a corresponding length of F2, and is oriented in a 5' to 3' direction towards H; and wherein $b^1$ and $c^1$ overlap by a length sufficient to permit annealing of their 5' ends to each other under conditions which allow a polymerase chain reaction (PCR) to be performed;

(iii) performing, in any desired order, PCR reactions with primers pairs A,B and C,D on the template prepared in (i) above; and (iv) mixing the products obtained in (iii) above and performing a PCR reaction using primers A and D.

2. A method according to claim 1 wherein F1 and F2 each encode at least one human antibody framework region, and optionally further CDRs.

3. A method according to claim 1 or 2 wherein H encodes a CDR of the said first antibody.

4. A method according to claim 1 wherein M encodes a non-human CDR region.

5. A method according to claim 4 wherein M encodes a murine or rodent CDR.

6. A method according to any claim 1 wherein the primers A and D contain at least one restriction endonuclease recognition site within 10 nucleotides of their 5' ends.

7. A method according to claim 1 wherein, in the primers B and C, $b^1$ and $c^1$ are the same number of nucleotides in length.

8. A method according to claim 1 wherein primers A, B, C and D are each from 15 to 200 nucleotides in length.

9. A method according to claim 8 wherein $a^1$, $b^2$, $c^2$ and $d^1$ of primers A, B, C and D respectively are each from 15 to 30 nucleotides in length.

* * * * *

UNITED STATES PATENT AND TRADEMARK OFFICE
CERTIFICATE OF CORRECTION

PATENT NO. : 5,858,725
DATED : January 12, 1999
INVENTOR(S) : CROWE et al

It is certified that error appears in the above-identified patent and that said Letters Patent is hereby corrected as shown below:

Column 37, line 58, delete "of".

Column 37, line 60, delete "is" and insert --are--.

Column 39, line 26, delete "primers" and insert --primer--.

Column 40, line 14, delete "any".

Signed and Sealed this

Sixth Day of July, 1999

Attest:

Attesting Officer

Q. TODD DICKINSON

Acting Commissioner of Patents and Trademarks

SEQUENCE LISTING ( 1 ) GENERAL INFORMATION:

( i i i ) NUMBER OF SEQUENCES: 31

( 2 ) INFORMATION FOR SEQ ID NO:1:

( i ) SEQUENCE CHARACTERISTICS:
  ( A ) LENGTH: 1457 base pairs
  ( B ) TYPE: nucleic acid
  ( C ) STRANDEDNESS: single
  ( D ) TOPOLOGY: linear ( i i ) MOLECULE TYPE: cDNA ( i i i ) HYPOTHETICAL: NO ( i v ) ANTI-SENSE: NO ( i x ) FEATURE:
  ( A ) NAME/KEY: MISC FEATURE
  ( B ) LOCATION: 156..182
  ( D ) OTHER INFORMATION: CAMPATH 1H FRH1

( i x ) FEATURE:
  ( A ) NAME/KEY: MISC FEATURE
  ( B ) LOCATION: 183..197
  ( D ) OTHER INFORMATION: CAMPATH 1H CDRH1

( i x ) FEATURE:
  ( A ) NAME/KEY: MISC FEATURE
  ( B ) LOCATION: 198..224
  ( D ) OTHER INFORMATION: CAMPATH 1H FRH2

( x i ) SEQUENCE DESCRIPTION: SEQ ID NO:1:

```
AAGCTTTACA  GTTACTGAGC  ACACAGGACC  TCACCATGNN  NNNNNNNNN   NNNNNNNNNN      60

NNNNNNNNNN  NNNNNNNNNN  NNNNNNNNNN  NNNNNNNNNN  NNNNNNNNNN  NNNNNNNNNN     120

NNNNNNNNNN  NNNNNNNNNN  NNNNNNNNNN  NNNNNTGCAC  CGTGTCTGGC  TTCACCTTCA     180

CCGATTTCTA  CATGAACTGG  GTGAGACAGC  CACCTGGACG  AGGTNNNNNN  NNNNNNNNNN     240

NNNNNNNNNN  NNNNNNNNNN  NNNNNNNNNN  NNNNNNNNNN  NNNNNNNNNN  NNNNNNNNNN     300

NNNNNNNNNN  NNNNNNNNNN  NNNNNNNNNN  NNNNNNNNNN  NNNNNNNNNN  NNNNNNNNNN     360

NNNNNNNNNN  NNNNNNNNNN  NNNNNNNNNN  NNNNNNNNNN  NNNNNNNNNN  NNNNNNNNNN     420

NNNNNNNNNN  NNNNNNNNNN  NNNNNNNNNN  NNNNNNNNNN  NNNNNNNNNN  NNNNNNNNNN     480

NNNNNNNNNN  NNNNNNNNNN  NNNNNNNNNN  NNNNNNNNNN  NNNNNNNNNN  NNNNNNNNNN     540

NNNNNNNNNN  NNNNNNNNNN  NNNNNNNNNN  NNNNNNNNNN  NNNNNNNNNN  NNNNNNNNNN     600

NNNNNNNNNN  NNNNNNNNNN  NNNNNNNNNN  NNNNNNNNNN  NNNNNNNNNN  NNNNNNNNNN     660

NNNNNNNNNN  NNNNNNNNNN  NNNNNNNNNN  NNNNNNNNNN  NNNNNNNNNN  NNNNNNNNNN     720

NNNNNNNNNN  NNNNNNNNNN  NNNNNNNNNN  NNNNNNNNNN  NNNNNNNNNN  NNNNNNNNNN     780
```

NNNNNNNNNN NNNNNNNNNN NNNNNNNNNN NNNNNNNNNN NNNNNNNNNN NNNNNNNNNN        840

NNNNNNNNNN NNNNNNNNNN NNNNNNNNNN NNNNNNNNNN NNNNNNNNNN NNNNNNNNNN        900

NNNNNNNNNN NNNNNNNNNN NNNNNNNNNN NNNNNNNNNN NNNNNNNNNN NNNNNNNNNN        960

NNNNNNNNNN NNNNNNNNNN NNNNNNNNNN NNNNNNNNNN NNNNNNNNNN NNNNNNNNNN       1020

NNNNNNNNNN NNNNNNNNNN NNNNNNNNNN NNNNNNNNNN NNNNNNNNNN NNNNNNNNNN       1080

NNNNNNNNNN NNNNNNNNNN NNNNNNNNNN NNNNNNNNNN NNNNNNNNNN NNNNNNNNNN       1140

NNNNNNNNNN NNNNNNNNNN NNNNNNNNNN NNNNNNNNNN NNNNNNNNNN NNNNNNNNNN       1200

NNNNNNNNNN NNNNNNNNNN NNNNNNNNNN NNNNNNNNNN NNNNNNNNNN NNNNNNNNNN       1260

NNNNNNNNNN NNNNNNNNNN NNNNNNNNNN NNNNNNNNNN NNNNNNNNNN NNNNNNNNNN       1320

NNNNNNNNNN NNNNNNNNNN NNNNNNNNNN NNNNNNNNNN NNNNNNNNNN NNNNNNNNNN       1380

NNNNNNNNNN NNNNNNNNNN NNNNNNNNNN NNNNNNNNNN NNNNNNNNNN CCGGGTAAAT       1440

GAGTGCGACG GAAGCTT                                                      1457

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: ssDNA ( i i i ) HYPOTHETICAL: NO ( i v ) ANTI-SENSE: NO ( x i ) SEQUENCE DESCRIPTION: SEQ ID NO:2:

GATCAAGCTT TACAGTTACT GAGC                                                24

( 2 ) INFORMATION FOR SEQ ID NO:3:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: ssDNA ( i i i ) HYPOTHETICAL: NO ( i v ) ANTI-SENSE: NO ( x i ) SEQUENCE DESCRIPTION: SEQ ID NO:3:

GCCCACACCC ATACCATAAG TGCTGAAGGT GCTGCCAGAC ACGGT                          45

( 2 ) INFORMATION FOR SEQ ID NO:4:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: ssDNA ( i i i ) HYPOTHETICAL: NO ( i v ) ANTI-SENSE: NO ( x i ) SEQUENCE DESCRIPTION: SEQ ID NO:4:

ACTTATGGTA TGGGTGTGGG CTGGGTGAGA CAGCCACCTG GACGA 45

(2) INFORMATION FOR SEQ ID NO:5:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: ssDNA (iii) HYPOTHETICAL: NO (iv) ANTI-SENSE: YES (xi) SEQUENCE DESCRIPTION: SEQ ID NO:5:

GATCAAGCTT CCGTCGCACT CATTTAC 27

(2) INFORMATION FOR SEQ ID NO:6:

(i) SEQUENCE CHARACTERISTICS:
        (A) LENGTH: 207 base pairs
        (B) TYPE: nucleic acid
        (C) STRANDEDNESS: single
        (D) TOPOLOGY: linear (ii) MOLECULE TYPE: dsDNA (xi) SEQUENCE DESCRIPTION: SEQ ID NO:6:

GATCAAGCTT TACAGTTACT GAGCACACAG GACCTCACCA TGNNNNNNNN NNNNNNNNNN 60
NNNNNNNNNN NNNNNNNNNN NNNNNNNNNN NNNNNNNNNN NNNNNNNNNN NNNNNNNNNN 120
NNNNNNNNNN NNNNNNNNNN NNNNNNNNNN NNNNNNNNT GCACCGTGTC TGGCAGCACC 180
TTCAGCACTT ATGGTATGGG TGTGGGC 207

(2) INFORMATION FOR SEQ ID NO:7:

(i) SEQUENCE CHARACTERISTICS:
        (A) LENGTH: 1285 base pairs
        (B) TYPE: nucleic acid
        (C) STRANDEDNESS: single
        (D) TOPOLOGY: linear (ii) MOLECULE TYPE: dsDNA (iii) HYPOTHETICAL: NO (iv) ANTI-SENSE: NO (xi) SEQUENCE DESCRIPTION: SEQ ID NO:7:

ACTTATGGTA TGGGTGTGGG CTGGGTGAGA CAGCCACCTG GACGAGGTNN NNNNNNNNNN 60
NNNNNNNNNN NNNNNNNNNN NNNNNNNNNN NNNNNNNNNN NNNNNNNNNN NNNNNNNNNN 120
NNNNNNNNNN NNNNNNNNNN NNNNNNNNNN NNNNNNNNNN NNNNNNNNNN NNNNNNNNNN 180
NNNNNNNNNN NNNNNNNNNN NNNNNNNNNN NNNNNNNNNN NNNNNNNNNN NNNNNNNNNN 240
NNNNNNNNNN NNNNNNNNNN NNNNNNNNNN NNNNNNNNNN NNNNNNNNNN NNNNNNNNNN 300
NNNNNNNNNN NNNNNNNNNN NNNNNNNNNN NNNNNNNNNN NNNNNNNNNN NNNNNNNNNN 360
NNNNNNNNNN NNNNNNNNNN NNNNNNNNNN NNNNNNNNNN NNNNNNNNNN NNNNNNNNNN 420
NNNNNNNNNN NNNNNNNNNN NNNNNNNNNN NNNNNNNNNN NNNNNNNNNN NNNNNNNNNN 480
NNNNNNNNNN NNNNNNNNNN NNNNNNNNNN NNNNNNNNNN NNNNNNNNNN NNNNNNNNNN 540
NNNNNNNNNN NNNNNNNNNN NNNNNNNNNN NNNNNNNNNN NNNNNNNNNN NNNNNNNNNN 600
NNNNNNNNNN NNNNNNNNNN NNNNNNNNNN NNNNNNNNNN NNNNNNNNNN NNNNNNNNNN 660

NNNNNNNNN NNNNNNNNN NNNNNNNNN NNNNNNNNN NNNNNNNNN NNNNNNNNN    720

NNNNNNNNN NNNNNNNNN NNNNNNNNN NNNNNNNNN NNNNNNNNN NNNNNNNNN    780

NNNNNNNNN NNNNNNNNN NNNNNNNNN NNNNNNNNN NNNNNNNNN NNNNNNNNN    840

NNNNNNNNN NNNNNNNNN NNNNNNNNN NNNNNNNNN NNNNNNNNN NNNNNNNNN    900

NNNNNNNNN NNNNNNNNN NNNNNNNNN NNNNNNNNN NNNNNNNNN NNNNNNNNN    960

NNNNNNNNN NNNNNNNNN NNNNNNNNN NNNNNNNNN NNNNNNNNN NNNNNNNNN   1020

NNNNNNNNN NNNNNNNNN NNNNNNNNN NNNNNNNNN NNNNNNNNN NNNNNNNNN   1080

NNNNNNNNN NNNNNNNNN NNNNNNNNN NNNNNNNNN NNNNNNNNN NNNNNNNNN   1140

NNNNNNNNN NNNNNNNNN NNNNNNNNN NNNNNNNNN NNNNNNNNN NNNNNNNNN   1200

NNNNNNNNN NNNNNNNNN NNNNNNNNN NNNNNNNNN NNNNNNNNN NNNNCCGGGT  1260

AAATGAGTGC GACGGAAGCT TGATC                                   1285

( 2 ) INFORMATION FOR SEQ ID NO:8:

( i ) SEQUENCE CHARACTERISTICS:
    ( A ) LENGTH: 1471 base pairs
    ( B ) TYPE: nucleic acid
    ( C ) STRANDEDNESS: single
    ( D ) TOPOLOGY: linear ( i i ) MOLECULE TYPE: dsDNA ( i x ) FEATURE:
    ( A ) NAME/KEY: MISC FEATURE
    ( B ) LOCATION: 160..186
    ( D ) OTHER INFORMATION: CAMPATH 1H FRH1

( i x ) FEATURE:
    ( A ) NAME/KEY: MISC FEATURE
    ( B ) LOCATION: 175..177
    ( D ) OTHER INFORMATION: POINT MUTATION ( i x ) FEATURE:
    ( A ) NAME/KEY: MISC FEATURE
    ( B ) LOCATION: 184..186
    ( D ) OTHER INFORMATION: POINT MUTATION ( i x ) FEATURE:
    ( A ) NAME/KEY: MISC FEATURE
    ( B ) LOCATION: 187..207
    ( D ) OTHER INFORMATION: DK48 CDRH1

( i x ) FEATURE:
    ( A ) NAME/KEY: MISC FEATURE
    ( B ) LOCATION: 208..234
    ( D ) OTHER INFORMATION: CAMPATH 1H FRH2

( x i ) SEQUENCE DESCRIPTION: SEQ ID NO:8:

GATCCAGCTT TACAGTTACT GAGCACACAG GACCTCACCA TGNNNNNNNN NNNNNNNNN    60

NNNNNNNNN NNNNNNNNN NNNNNNNNN NNNNNNNNN NNNNNNNNN NNNNNNNNN    120

NNNNNNNNN NNNNNNNNN NNNNNNNNN NNNNNNNNT GCACCGTGTC TGGCAGCACC    180

TTCAGCACTT ATGGTATGGG TGTGGGCTGG GTGAGACAGC CACCTGGACG AGGTNNNNN    240

NNNNNNNNN NNNNNNNNN NNNNNNNNN NNNNNNNNN NNNNNNNNN NNNNNNNNN    300

NNNNNNNNN NNNNNNNNN NNNNNNNNN NNNNNNNNN NNNNNNNNN NNNNNNNNN    360

NNNNNNNNN NNNNNNNNN NNNNNNNNN NNNNNNNNN NNNNNNNNN NNNNNNNNN    420

NNNNNNNNN NNNNNNNNN NNNNNNNNN NNNNNNNNN NNNNNNNNN NNNNNNNNN    480

NNNNNNNNN NNNNNNNNN NNNNNNNNN NNNNNNNNN NNNNNNNNN NNNNNNNNN    540

NNNNNNNNN NNNNNNNNN NNNNNNNNN NNNNNNNNN NNNNNNNNN NNNNNNNNN    600

| | | | | | | |
|---|---|---|---|---|---|---|
| NNNNNNNNNN | NNNNNNNNNN | NNNNNNNNNN | NNNNNNNNNN | NNNNNNNNNN | NNNNNNNNNN | 660 |
| NNNNNNNNNN | NNNNNNNNNN | NNNNNNNNNN | NNNNNNNNNN | NNNNNNNNNN | NNNNNNNNNN | 720 |
| NNNNNNNNNN | NNNNNNNNNN | NNNNNNNNNN | NNNNNNNNNN | NNNNNNNNNN | NNNNNNNNNN | 780 |
| NNNNNNNNNN | NNNNNNNNNN | NNNNNNNNNN | NNNNNNNNNN | NNNNNNNNNN | NNNNNNNNNN | 840 |
| NNNNNNNNNN | NNNNNNNNNN | NNNNNNNNNN | NNNNNNNNNN | NNNNNNNNNN | NNNNNNNNNN | 900 |
| NNNNNNNNNN | NNNNNNNNNN | NNNNNNNNNN | NNNNNNNNNN | NNNNNNNNNN | NNNNNNNNNN | 960 |
| NNNNNNNNNN | NNNNNNNNNN | NNNNNNNNNN | NNNNNNNNNN | NNNNNNNNNN | NNNNNNNNNN | 1020 |
| NNNNNNNNNN | NNNNNNNNNN | NNNNNNNNNN | NNNNNNNNNN | NNNNNNNNNN | NNNNNNNNNN | 1080 |
| NNNNNNNNNN | NNNNNNNNNN | NNNNNNNNNN | NNNNNNNNNN | NNNNNNNNNN | NNNNNNNNNN | 1140 |
| NNNNNNNNNN | NNNNNNNNNN | NNNNNNNNNN | NNNNNNNNNN | NNNNNNNNNN | NNNNNNNNNN | 1200 |
| NNNNNNNNNN | NNNNNNNNNN | NNNNNNNNNN | NNNNNNNNNN | NNNNNNNNNN | NNNNNNNNNN | 1260 |
| NNNNNNNNNN | NNNNNNNNNN | NNNNNNNNNN | NNNNNNNNNN | NNNNNNNNNN | NNNNNNNNNN | 1320 |
| NNNNNNNNNN | NNNNNNNNNN | NNNNNNNNNN | NNNNNNNNNN | NNNNNNNNNN | NNNNNNNNNN | 1380 |
| NNNNNNNNNN | NNNNNNNNNN | NNNNNNNNNN | NNNNNNNNNN | NNNNNNNNNN | NNNNNNNNNN | 1440 |
| CCGGGTAAAT | GAGTGCGACG | GAAGCTTGAT | C | | | 1471 |

(2) INFORMATION FOR SEQ ID NO:9:

( i ) SEQUENCE CHARACTERISTICS:
        ( A ) LENGTH: 417 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( a ) ORGANISM: Rattus rattus ( i x ) FEATURE:
        ( A ) NAME/KEY: CDS
        ( B ) LOCATION: 1..417
        ( D ) OTHER INFORMATION: Heavy chain variable region with
            signal sequence. YFC51.1.1

( i x ) FEATURE:
        ( A ) NAME/KEY: MISC SIGNAL
        ( B ) LOCATION: 1..57
        ( D ) OTHER INFORMATION: Signal Sequence ( i x ) FEATURE:
        ( A ) NAME/KEY: MISC FEATURE
        ( B ) LOCATION: 148..162
        ( D ) OTHER INFORMATION: CDR 1

( i x ) FEATURE:
        ( A ) NAME/KEY: MISC FEATURE
        ( B ) LOCATION: 205..255

( i x ) FEATURE:
        ( A ) NAME/KEY: MISC FEATURE
        ( B ) LOCATION: 352..384

( x i ) SEQUENCE DESCRIPTION: SEQ ID NO:9:

| | | | | | | | | | | | | | | | |
|---|---|---|---|---|---|---|---|---|---|---|---|---|---|---|---|
| ATG | AAA | TGC | AGC | TGG | ATC | AAC | CTC | TTC | TTG | ATG | GCA | CTA | GCT | TCA | GGG | 48 |
| Met | Lys | Cys | Ser | Trp | Ile | Asn | Leu | Phe | Leu | Met | Ala | Leu | Ala | Ser | Gly | |
| 1 | | | | 5 | | | | | 10 | | | | | 15 | | |
| GTC | TAC | GCA | GAA | GTG | CAG | CTG | CAA | CAG | TCT | GGG | CCC | GAG | CTT | CGG | AGA | 96 |
| Val | Tyr | Ala | Glu | Val | Gln | Leu | Gln | Gln | Ser | Gly | Pro | Glu | Leu | Arg | Arg | |
| | | | 20 | | | | 25 | | | | | 30 | | | | |
| CCT | GGG | TCC | TCA | GTC | AAG | TTG | TCT | TGT | AAG | ACT | TCT | GGC | TAC | AGC | ATT | 144 |

| | | | | | | | | | | | | | | | |
|---|---|---|---|---|---|---|---|---|---|---|---|---|---|---|---|
| Pro | Gly | Ser | Ser | Val | Lys | Leu | Ser | Cys | Lys | Thr | Ser | Gly | Tyr | Ser | Ile |
| | | 35 | | | | 40 | | | | | | 45 | | | |

| AAA | GAT | TAC | CTT | CTG | CAC | TGG | GTA | AAA | CAT | AGG | CCA | GAA | TAC | GGC | CTG | 192 |
|---|---|---|---|---|---|---|---|---|---|---|---|---|---|---|---|---|
| Lys | Asp | Tyr | Leu | Leu | His | Trp | Val | Lys | His | Arg | Pro | Glu | Tyr | Gly | Leu | |
| | 50 | | | | | 55 | | | | | 60 | | | | | |

| GAA | TGG | ATA | GGA | TGG | ATT | GAT | CCT | GAG | GAT | GGT | GGA | ACA | AAG | TAT | GGT | 240 |
|---|---|---|---|---|---|---|---|---|---|---|---|---|---|---|---|---|
| Glu | Trp | Ile | Gly | Trp | Ile | Asp | Pro | Glu | Asp | Gly | Gly | Thr | Lys | Tyr | Gly | |
| 65 | | | | | 70 | | | | | 75 | | | | | 80 | |

| CAG | AAG | TTT | CAA | AGC | AGG | GCC | ACA | CTC | ACT | GCA | GAT | ACA | TCC | TCC | AAC | 288 |
|---|---|---|---|---|---|---|---|---|---|---|---|---|---|---|---|---|
| Gln | Lys | Phe | Gln | Ser | Arg | Ala | Thr | Leu | Thr | Ala | Asp | Thr | Ser | Ser | Asn | |
| | | | | 85 | | | | | 90 | | | | | 95 | | |

| ACA | GCC | TAC | ATG | CAA | CTC | AGC | AGC | CTG | ACG | TCT | GAC | GAC | ACA | GCA | ACC | 336 |
|---|---|---|---|---|---|---|---|---|---|---|---|---|---|---|---|---|
| Thr | Ala | Tyr | Met | Gln | Leu | Ser | Ser | Leu | Thr | Ser | Asp | Asp | Thr | Ala | Thr | |
| | | | 100 | | | | | 105 | | | | | 110 | | | |

| TAT | TTT | TGT | ACT | AGA | GGC | GAA | TAT | AGA | TAC | AAC | TCG | TGG | TTT | GAT | TAC | 384 |
|---|---|---|---|---|---|---|---|---|---|---|---|---|---|---|---|---|
| Tyr | Phe | Cys | Thr | Arg | Gly | Glu | Tyr | Arg | Tyr | Asn | Ser | Trp | Phe | Asp | Tyr | |
| | | 115 | | | | | 120 | | | | | 125 | | | | |

| TGG | GGC | CAA | GGC | ACT | CTG | GTC | ACT | GTC | TCT | TCA | | | | | | 417 |
|---|---|---|---|---|---|---|---|---|---|---|---|---|---|---|---|---|
| Trp | Gly | Gln | Gly | Thr | Leu | Val | Thr | Val | Ser | Ser | | | | | | |
| 130 | | | | | 135 | | | | | | | | | | | |

( 2 ) INFORMATION FOR SEQ ID NO:10:

( i ) SEQUENCE CHARACTERISTICS:
        ( A ) LENGTH: 139 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

| Met | Lys | Cys | Ser | Trp | Ile | Asn | Leu | Phe | Leu | Met | Ala | Leu | Ala | Ser | Gly |
|---|---|---|---|---|---|---|---|---|---|---|---|---|---|---|---|
| 1 | | | | 5 | | | | | 10 | | | | | 15 | |

| Val | Tyr | Ala | Glu | Val | Gln | Leu | Gln | Gln | Ser | Gly | Pro | Glu | Leu | Arg | Arg |
|---|---|---|---|---|---|---|---|---|---|---|---|---|---|---|---|
| | | | 20 | | | | | 25 | | | | | 30 | | |

| Pro | Gly | Ser | Ser | Val | Lys | Leu | Ser | Cys | Lys | Thr | Ser | Gly | Tyr | Ser | Ile |
|---|---|---|---|---|---|---|---|---|---|---|---|---|---|---|---|
| | | | 35 | | | | 40 | | | | | 45 | | | |

| Lys | Asp | Tyr | Leu | Leu | His | Trp | Val | Lys | His | Arg | Pro | Glu | Tyr | Gly | Leu |
|---|---|---|---|---|---|---|---|---|---|---|---|---|---|---|---|
| | 50 | | | | | 55 | | | | | 60 | | | | |

| Glu | Trp | Ile | Gly | Trp | Ile | Asp | Pro | Glu | Asp | Gly | Gly | Thr | Lys | Tyr | Gly |
|---|---|---|---|---|---|---|---|---|---|---|---|---|---|---|---|
| 65 | | | | | 70 | | | | | 75 | | | | | 80 |

| Gln | Lys | Phe | Gln | Ser | Arg | Ala | Thr | Leu | Thr | Ala | Asp | Thr | Ser | Ser | Asn |
|---|---|---|---|---|---|---|---|---|---|---|---|---|---|---|---|
| | | | | 85 | | | | | 90 | | | | | 95 | |

| Thr | Ala | Tyr | Met | Gln | Leu | Ser | Ser | Leu | Thr | Ser | Asp | Asp | Thr | Ala | Thr |
|---|---|---|---|---|---|---|---|---|---|---|---|---|---|---|---|
| | | | 100 | | | | | 105 | | | | | 110 | | |

| Tyr | Phe | Cys | Thr | Arg | Gly | Glu | Tyr | Arg | Tyr | Asn | Ser | Trp | Phe | Asp | Tyr |
|---|---|---|---|---|---|---|---|---|---|---|---|---|---|---|---|
| | | 115 | | | | | 120 | | | | | 125 | | | |

| Trp | Gly | Gln | Gly | Thr | Leu | Val | Thr | Val | Ser | Ser |
|---|---|---|---|---|---|---|---|---|---|---|
| | 130 | | | | | 135 | | | | |

( 2 ) INFORMATION FOR SEQ ID NO:11:

( i ) SEQUENCE CHARACTERISTICS:
        ( A ) LENGTH: 375 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( a ) ORGANISM: Rattus rattus ( i x ) FEATURE:
  ( A ) NAME/KEY: CDS
  ( B ) LOCATION: 1..375
  ( D ) OTHER INFORMATION: Light chain variable region with
    signal sequence. YFC51.1.1

( i x ) FEATURE:
  ( A ) NAME/KEY: MISC SIGNAL
  ( B ) LOCATION: 1..60
  ( D ) OTHER INFORMATION: Signal Sequence ( i x ) FEATURE:
  ( A ) NAME/KEY: MISC FEATURE
  ( B ) LOCATION: 130..162
  ( D ) OTHER INFORMATION: CDR 1

( i x ) FEATURE:
  ( A ) NAME/KEY: MISC FEATURE
  ( B ) LOCATION: 208..228
  ( D ) OTHER INFORMATION: CDR 2

( i x ) FEATURE:
  ( A ) NAME/KEY: MISC FEATURE
  ( B ) LOCATION: 325..351
  ( D ) OTHER INFORMATION: CDR 3

( x i ) SEQUENCE DESCRIPTION: SEQ ID NO:11:

```
ATG AGG GTC CAG GTT CAG TTT CTG GGG CTC CTT CTG CTC TGG ACA TCA      48
Met Arg Val Gln Val Gln Phe Leu Gly Leu Leu Leu Leu Trp Thr Ser
 1           5                   10                  15

GGT GCC CAG TGT GAT GTC CAG ATG ACC CAG TCT CCG TCT TAT CTT GCT      96
Gly Ala Gln Cys Asp Val Gln Met Thr Gln Ser Pro Ser Tyr Leu Ala
             20                  25                  30

GCG TCT CCT GGA GAA AGT GTT TCC ATC AGT TGC AAG GCA AGT AAG AGC     144
Ala Ser Pro Gly Glu Ser Val Ser Ile Ser Cys Lys Ala Ser Lys Ser
         35                  40                  45

ATT AGC AAT TAT TTA GCC TGG TAT CAA CAG AAA CCT GGG GAA GCA AAT     192
Ile Ser Asn Tyr Leu Ala Trp Tyr Gln Gln Lys Pro Gly Glu Ala Asn
     50                  55                  60

AAA CTT CTT GTC TAT TAT GGG TCA ACT TTG CGA TCT GGA ATT CCA TCG     240
Lys Leu Leu Val Tyr Tyr Gly Ser Thr Leu Arg Ser Gly Ile Pro Ser
 65                  70                  75                  80

AGG TTC AGT GGC AGT GGA TCT GGT ACA GAT TTC ACT CTC ACC ATC AGA     288
Arg Phe Ser Gly Ser Gly Ser Gly Thr Asp Phe Thr Leu Thr Ile Arg
                 85                  90                  95

AAC CTG GAG CCT GCA GAT TTT GCA GTC TAC TAC TGT CAA CAG TAT TAT     336
Asn Leu Glu Pro Ala Asp Phe Ala Val Tyr Tyr Cys Gln Gln Tyr Tyr
             100                 105                 110

GAA AGA CCG CTC ACG TTC GGT TCT GGG ACC AAG CTG GAG                 375
Glu Arg Pro Leu Thr Phe Gly Ser Gly Thr Lys Leu Glu
         115                 120                 125
```

( 2 ) INFORMATION FOR SEQ ID NO:12:

( i ) SEQUENCE CHARACTERISTICS:
    ( A ) LENGTH: 125 amino acids
    ( B ) TYPE: amino acid
    ( D ) TOPOLOGY: linear ( i i ) MOLECULE TYPE: protein ( x i ) SEQUENCE DESCRIPTION: SEQ ID NO:12:

```
Met Arg Val Gln Val Gln Phe Leu Gly Leu Leu Leu Leu Trp Thr Ser
 1           5                   10                  15

Gly Ala Gln Cys Asp Val Gln Met Thr Gln Ser Pro Ser Tyr Leu Ala
             20                  25                  30

Ala Ser Pro Gly Glu Ser Val Ser Ile Ser Cys Lys Ala Ser Lys Ser
         35                  40                  45
```

```
Ile Ser Asn Tyr Leu Ala Trp Tyr Gln Gln Lys Pro Gly Glu Ala Asn
     50                  55                  60

Lys Leu Leu Val Tyr Tyr Gly Ser Thr Leu Arg Ser Gly Ile Pro Ser
 65              70                  75                      80

Arg Phe Ser Gly Ser Gly Ser Gly Thr Asp Phe Thr Leu Thr Ile Arg
                 85                  90                  95

Asn Leu Glu Pro Ala Asp Phe Ala Val Tyr Tyr Cys Gln Gln Tyr Tyr
            100                 105             110

Glu Arg Pro Leu Thr Phe Gly Ser Gly Thr Lys Leu Glu
            115                 120             125
```

(2) INFORMATION FOR SEQ ID NO:13:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: ssDNA (iii) HYPOTHETICAL: NO (iv) ANTI-SENSE: NO (xi) SEQUENCE DESCRIPTION: SEQ ID NO:13:

GATCAAGCTT CTCTACAGTT ACTGAGCACA 30

(2) INFORMATION FOR SEQ ID NO:14:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: ssDNA (iii) HYPOTHETICAL: NO (iv) ANTI-SENSE: YES (xi) SEQUENCE DESCRIPTION: SEQ ID NO:14:

GCTAAATAAT TGCTAATGCT CTTACTTGCT TTACAGGTGA TGG 43

(2) INFORMATION FOR SEQ ID NO:15:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: ssDNA (iii) HYPOTHETICAL: NO (iv) ANTI-SENSE: NO (xi) SEQUENCE DESCRIPTION: SEQ ID NO:15:

AGAGCATTAG CAATTATTTA GCCTGGTACC AGCAGAAGCC AGG 43

(2) INFORMATION FOR SEQ ID NO:16:

(i) SEQUENCE CHARACTERISTICS:
        (A) LENGTH: 41 base pairs
        (B) TYPE: nucleic acid
        (C) STRANDEDNESS: single (D) TOPOLOGY: linear (ii) MOLECULE TYPE: ssDNA (iii) HYPOTHETICAL: NO (iv) ANTI-SENSE: YES (xi) SEQUENCE DESCRIPTION: SEQ ID NO:16:

AGATCGCAAA GTTGACCCAT AGTAGATCAG CAGCTTTGGA G    41

(2) INFORMATION FOR SEQ ID NO:17:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: ssDNA (iii) HYPOTHETICAL: NO (iv) ANTI-SENSE: NO (xi) SEQUENCE DESCRIPTION: SEQ ID NO:17:

TATGGGTCAA CTTTGCGATC TGGTGTGCCA AGCAGATTCA G    41

(2) INFORMATION FOR SEQ ID NO:18:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: ssDNA (iii) HYPOTHETICAL: NO (iv) ANTI-SENSE: YES (xi) SEQUENCE DESCRIPTION: SEQ ID NO:18:

CGTGAGCGGT CTTTCATAAT ACTGTTGGCA GTAGTAGGTG GCGATGT    47

(2) INFORMATION FOR SEQ ID NO:19:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: ssDNA (iii) HYPOTHETICAL: NO (iv) ANTI-SENSE: NO (xi) SEQUENCE DESCRIPTION: SEQ ID NO:19:

CAACAGTATT ATGAAAGACC GCTCACGTTC GGCCAAGGGA CCAAGGT    47

(2) INFORMATION FOR SEQ ID NO:20:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: ssDNA ( i i i ) HYPOTHETICAL: NO ( i v ) ANTI-SENSE: YES ( x i ) SEQUENCE DESCRIPTION: SEQ ID NO:20:

GATCAAGCTT CTAACACTCT CCCCTGTTGA 30

( 2 ) INFORMATION FOR SEQ ID NO:21:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: ssDNA ( i i i ) HYPOTHETICAL: NO ( i v ) ANTI-SENSE: NO ( x i ) SEQUENCE DESCRIPTION: SEQ ID NO:21:

TGGGATCGAT CAAGCTTTAC AGTTACTGAG C 31

( 2 ) INFORMATION FOR SEQ ID NO:22:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: ssDNA ( i i i ) HYPOTHETICAL: NO ( i v ) ANTI-SENSE: YES ( x i ) SEQUENCE DESCRIPTION: SEQ ID NO:22:

GTGCAGAAGG TAATCGGTGA AGGTGAAGCC AGACAC 36

( 2 ) INFORMATION FOR SEQ ID NO:23:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: ssDNA ( i i i ) HYPOTHETICAL: NO ( i v ) ANTI-SENSE: NO ( x i ) SEQUENCE DESCRIPTION: SEQ ID NO:23:

GATTACCTTC TGCACTGGGT GAGACAGCCA CCTGGA 36

( 2 ) INFORMATION FOR SEQ ID NO:24:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: ssDNA ( i i i ) HYPOTHETICAL: NO ( i v ) ANTI-SENSE: YES ( x i ) SEQUENCE DESCRIPTION: SEQ ID NO:24:

ATACTTTGTT TCACCATCCT CAGGATCAAT CCATCCAATC CACTCAAGAC CTCG    54

( 2 ) INFORMATION FOR SEQ ID NO:25:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: ssDNA ( i i i ) HYPOTHETICAL: NO ( i v ) ANTI-SENSE: NO ( x i ) SEQUENCE DESCRIPTION: SEQ ID NO:25:

GGTGAAACAA AGTATGGTCA GAAGTTTCAA AGCAGAGTGA CAATGCTGGT AGAC    54

( 2 ) INFORMATION FOR SEQ ID NO:26:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: ssDNA ( i i i ) HYPOTHETICAL: NO ( i v ) ANTI-SENSE: YES ( x i ) SEQUENCE DESCRIPTION: SEQ ID NO:26:

CCACGAGTTG TATCTATATT CGCCTCTTGC ACAATAATAG ACCGC    45

( 2 ) INFORMATION FOR SEQ ID NO:27:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: ssDNA ( i i i ) HYPOTHETICAL: NO ( i v ) ANTI-SENSE: NO ( x i ) SEQUENCE DESCRIPTION: SEQ ID NO:27:

AGATACAACT CGTGGTTTGA TTACTGGGGT CAAGGCTCAC TAGTCACAGT CTCC    54

( 2 ) INFORMATION FOR SEQ ID NO:28:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: ssDNA ( i i i ) HYPOTHETICAL: NO ( i v ) ANTI-SENSE: YES ( x i ) SEQUENCE DESCRIPTION: SEQ ID NO:28:

TAGAGTCCTG AGGGAATTCG GACAGCCGGG AAGGTG    36

(2) INFORMATION FOR SEQ ID NO:29:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: ssDNA (iii) HYPOTHETICAL: NO (iv) ANTI-SENSE: NO (xi) SEQUENCE DESCRIPTION: SEQ ID NO:29:

GCTGCTCCTT TTAAGCTTTG GGGTCAAGGC TCACTAGTCA CAGTCTCC    48

(2) INFORMATION FOR SEQ ID NO:30:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: ssDNA (iii) HYPOTHETICAL: NO (iv) ANTI-SENSE: YES (xi) SEQUENCE DESCRIPTION: SEQ ID NO:30:

AAGCTTCCGT CGAATTCATT TACCCGGAGA CAG    33

(2) INFORMATION FOR SEQ ID NO:31:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: ssDNA (iii) HYPOTHETICAL: NO (iv) ANTI-SENSE: NO (vi) ORIGINAL SOURCE:
        ORIGANISM: Rattus rattus (xi) SEQUENCE DESCRIPTION: SEQ ID NO:31:

AGTGGATAGA CAGATGGGGC    20